US009248200B2

(12) United States Patent
Ying et al.

(10) Patent No.: US 9,248,200 B2
(45) Date of Patent: Feb. 2, 2016

(54) METHOD OF DELIVERING AN ANTI-CANCER AGENT TO A CELL

(75) Inventors: Jackie Y. Ying, Singapore (SG); Joo Eun Chung, Singapore (SG); Motoichi Kurisawa, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 138 days.

(21) Appl. No.: 12/739,668

(22) PCT Filed: Oct. 23, 2008

(86) PCT No.: PCT/SG2008/000409
§ 371 (c)(1),
(2), (4) Date: Aug. 20, 2010

(87) PCT Pub. No.: WO2009/054813
PCT Pub. Date: Apr. 30, 2009

(65) Prior Publication Data
US 2011/0044992 A1    Feb. 24, 2011

Related U.S. Application Data

(60) Provisional application No. 60/960,969, filed on Oct. 23, 2007.

(51) Int. Cl.
| A61K 9/51 | (2006.01) |
| A61K 47/48 | (2006.01) |
| A61K 9/107 | (2006.01) |
| A61K 31/353 | (2006.01) |
| B82Y 5/00 | (2011.01) |
| C08B 37/08 | (2006.01) |
| C08G 65/331 | (2006.01) |
| C08G 65/332 | (2006.01) |
| A61K 39/00 | (2006.01) |

(52) U.S. Cl.
CPC ......... *A61K 47/48846* (2013.01); *A61K 9/1075* (2013.01); *A61K 31/353* (2013.01); *B82Y 5/00* (2013.01); *C08B 37/0072* (2013.01); *C08G 65/3317* (2013.01); *C08G 65/3326* (2013.01); *A61K 2039/505* (2013.01); *C08L 2203/02* (2013.01)

(58) Field of Classification Search
USPC ............ 424/78.3, 78.31, 78.08; 977/906, 788
See application file for complete search history.

(56) References Cited

U.S. PATENT DOCUMENTS

| 7,858,080 | B2 * | 12/2010 | Chung et al. | ................. | 424/78.3 |
| 8,138,163 | B2 * | 3/2012 | Chung et al. | ..................... | 514/54 |
| 8,541,016 | B2 * | 9/2013 | Kurisawa et al. | ............. | 424/425 |
| 2008/0102052 | A1 | 5/2008 | Chung et al. | | |
| 2013/0004488 | A1 * | 1/2013 | Kurisawa et al. | .......... | 424/133.1 |

FOREIGN PATENT DOCUMENTS

| WO | 2006124000 A1 | 11/2006 | | |
| WO | WO 2006/124000 A1 * | 11/2006 | ............... | C08B 37/08 |

OTHER PUBLICATIONS

NCBI PubChem-Flavopiridol.*
Wiesenthal, (Human Tumor Assay Journal, on-line at (http://weisenthal.org/synergy1.htm, Mar. 14, 2012).*
Berenbaum (Clin exp Immunol, 1997, 28:1-18).*
International Preliminary Report on Patentability (date of mailing Mar. 9, 2010) issued in corresponding PCT Application No. PCT/SG2008/000409.
Written Opinion dated Oct. 13, 2009 issued in corresponding PCT Application No. PCT/SG2008/000409.
Written Opinion dated Jan. 7, 2010 issued in corresponding PCT Application No. PCT/SG2008/000409.
1st Office Action, dated Jul. 26, 2011, issued in corresponding Chinese Patent Application No. 200880122383.2.
2nd Office Action, dated May 24, 2012, issued in corresponding Chinese Patent Application No. 200880122383.2.
Ariga, T. and Hamano M., "Radical Scavenging Action and Its Mode in Procyanidins B-1 and B-3 from Azuki Beans to Peroxyl Radicals", Agricultural and Biological Chemistry, 1990, pp. 2499-2504, vol. 54, Issue 10.
Bordoni, A. et al., "Green tea protection of hypoxia/reoxygenation injury in cultured cardiac cells", The Journal of Nutritional Biochemistry, Feb. 2002, pp. 103-111, vol. 13, Issue 2.
Cao, Y. and Cao, R., "Angiogenesis inhibited by drinking tea", Nature, Apr. 1, 1999, p. 381, vol. 398, No. 6726.
Chung, J.E. et al., "Amplification of Antioxidant Activity of Catechin by Polycondensation with Acetaldehyde", Biomacromolecules, Jan. 2004, pp. 113-118, vol. 5, Issue 1.
Duncan, R., "The dawning era of polymer therapeutics", Nature Reviews Drug Discovery, May 2003, pp. 347-360, vol. 2, Issue 5.
Farokhzad, O.C. et al., "Nanoparticle-aptamer bioconjugates: A new approach for targeting prostate cancer cells", Cancer Research, Nov. 1, 2004, pp. 7668-7672, vol. 64, Issue 21.
Garbisa, S. et al., "Tumor invasion: Molecular shears blunted by green tea", Nature Medicine, Nov. 1999, p. 1216, vol. 5, Issue 11.
Gordon, A.N. et al., "Recurrent epithelial ovarian carcinoma: A randomized phase III study of pegylated liposomal doxorubicin versus topotecan", Journal of Clinical Oncology, Jul. 15, 2001, pp. 3312-3322, vol. 19, Issue 14.
Gref, R. et al., "Biodegradable long-circulating polymeric nanospheres", Science, Mar. 18, 1994, pp. 1600-1603, vol. 263, No. 5153.
Hagerman, A.E. et al., "High Molecular Weight Plant Polyphenolics (Tannins) as Biological Antioxidants", Journal of Agricultural and Food Chemistry, May 1998, pp. 1887-1892, vol. 46, Issue 5.
Hubbell, J.A., "Materials Science: Enhancing drug function", Science, Apr. 25, 2003, pp. 595-596, vol. 300, No. 5619.
Ikeda, I. et al., "Tea Catechins with a Galloyl Moiety Suppress Postprandial Hypertriacylglycerolemia by Delaying Lymphatic Transport of Dietary Fat in Rats", The Journal of Nutrition, Feb. 2000, pp. 155-159, vol. 135, Issue 2.
Isemura, M. et al., Tea catechins and related polyphenols as anti-cancer agents, BioFactors, 2000, pp. 81-85, vol. 13, , Issue 1-4.

(Continued)

*Primary Examiner* — Yan Xiao
(74) *Attorney, Agent, or Firm* — Klarquist Sparkman, LLP

(57) ABSTRACT

There is provided a delivery vehicle comprising an anti-cancer agent together with a conjugate of a delivery agent containing a free aldehyde and a flavonoid, having the delivery agent conjugated at the C6 and/or the C8 position of the A ring of the flavonoid. The resulting delivery vehicles may be used to deliver an anti-cancer agent to a cell.

15 Claims, 7 Drawing Sheets

(56) References Cited

OTHER PUBLICATIONS

Jankun, J. et al., "Why drinking green tea could prevent cancer", Nature, Jun. 5, 1997, p. 561, vol. 387, No. 6633.
Kakizawa, Y. and Kataoka, K., "Block copolymer micelles for delivery of gene and related compounds", Advanced Drug Delivery Reviews, Feb. 21, 2002, pp. 203-222, vol. 54, Issue 2.
Kataoka, K. et al., "Block copolymer micelles as vehicles for drug delivery", Journal of Controlled Release, May 1, 1993, pp. 119-132, vol. 24, Issues 1-3.
Kopecek, J. et al., "HPMA copolymer-anticancer drug conjugates: Design, activity, and mechanism of action", European Journal of Pharmaceutics and Biopharmaceutics, Jul. 3, 2000, pp. 61-81, vol. 50, Issue 1.
Kurisawa, M. et al., "Enzymatic Synthesis and Antioxidant Properties of Poly(rutin)", Biomacromolecules, Sep. 2003, pp. 1394-1399, vol. 4, Issue 5.
Kuroda, Y. and Hara, Y., "Antimutagenic and anticarcinogenic activity of tea polyphenols", Mutation Research, Jan. 1999, pp. 69-97, vol. 436, Issue 1.
Kuzuhara, T. et al., "DNA and RNA as new binding targets of green tea catechins", The Journal of Biological Chemistry, Jun. 23, 2006, pp. 17446-17456, vol. 281, Issue 25.
Lee, E.S. et al., "Polymeric micelle for tumor pH and folate-mediated targeting", Journal of Controlled Release, Aug. 28, 2003, pp. 103-113, vol. 91, Issues 1-2.
Li, C. and Xie, B., "Evaluation of the Antioxidant and Pro-oxidant Effects of Tea Catechin Oxypolymers", Journal of Agricultural and Food Chemistry, Dec. 2000, pp. 6362-6366, vol. 48, Issue 12.
Lill, G. et al., "Complex effects of different green tea catechins on human platelets", FEBS Letters, Jul. 10, 2003, pp. 265-270, vol. 546, Issues 2-3.
Matsumura, Y. and Maeda, H., "A new concept for macromolecular therapeutics in cancer chemotherapy: Mechanism of tumoritropic accumulation of proteins and the antitumor agent smancs", Cancer Research, Dec. 1986, pp. 6387-6392, vol. 46, Issue 12 Part 1.
Mei, Y. et al., "Reversal of cancer multidrug resistance by green tea polyphenols", Journal of Pharmacy and Pharmacology, Oct. 2004, pp. 1307-1314, vol. 56, Issue 10.
Nakagawa, K. et al., "Tea Catechin Supplementation Increases Antioxidant Capacity and Prevents Phospholipid Hydroperoxidation in Plasma of Humans", Journal of Agricultural and Food Chemistry, Oct. 1999, pp. 3967-3973, vol. 47, Issue 10.
Nance, C.L. and Shearer, W.T., "Is green tea good for HIC-1 infection?", Journal of Allergy and Clinical Immunology, Nov. 2003, pp. 851-853, vol. 112, Issue 5.
Otsuka, H. et al., "PEGylated nanoparticles for biological and pharmaceutical applications", Advanced Drug Delivery Reviews, Feb. 24, 2003, pp. 403-419, vol. 55, Issue 3.
Roedig-Penman A. and Gordon, M.H., "Antioxidant Properties of Catechins and Green Tea Extracts in Model Food Emulsions", Journal of Agricultural and Food Chemistry, Nov. 1997, pp. 4267-4270, vol. 45, Issue 11.
Sakanaka, S. and Okada, Y., "Inhibitory Effects of Green Tea Polyphenols on the Production of a Virulence Factor of the Periodontal-Disease-Causing Anaerobic Bacterium Porphyromonas gingivalis", Journal of Agricultural and Food Chemistry, Mar. 24, 2004, pp. 1688-1692, vol. 52, Issue 6.
Tachibana, H. et al., "A receptor for green tea polyphenol EGCG", Nature Structural & Molecular Biology, Apr. 2004, pp. 380-381, vol. 11, Issue 4.
Terao, J. et al., Arch. Biochem. Biophys., 1994, pp. 278-284, vol. 308.
Wu, K. et al., "Flavopriridol and Trastuzumab Synergistically Inhibit Proliferation of Breast Cancer Cells: Association with Selective Cooperative Inhibition of Cyclin D1-dependent Kinase and Akt Signaling Pathways", Molecular Cancer Therapeutics, Jul. 2002, pp. 695-706, vol. 1, Issue 9.
Yamanaka, N. et al., "Green tea catechins such as (−)-epicatechin and (−)-epigallocatechin accelerate Cu2+-induced low density lipoprotein oxidation in propagation phase", FEBS Letters, Jan. 20, 1997, pp. 230-234, vol. 401, Issues 2-3.
Yang, C.S. and Wang, Z.-Y., "Tea and cancer", Journal of the National Cancer Institute, Jul. 7, 1993, pp. 1038-1049, vol. 85, No. 13.
Yen, G.C. et al., "Antioxidant and Pro-Oxidant Effects of Various Tea Extracts", Journal of Agricultural and Food Chemistry, Jan. 1997, pp. 30-34, vol. 45, Issue 1.
Yokozawa, T. et al., "Antioxidative Activity of Green Tea Treated with Radical Initiator 2,2'-Azobis(2-amidinopropane) Dihydrochloride", Journal of Agricultural and Food Chemistry, Oct. 2000, pp. 5068-5073, vol. 48, Issue 10.
Zhao, J. et al., "Anti-tumor-promoting activity of a polyphenolic fraction isolated from grape seeds in the mouse skin two-stage initiation-promotion protocol and identification of procyanidin B5-3'-gallate as the most effective antioxidant constituent", Carcinogenesis, Sep. 1999, pp. 1737-1745, vol. 20, Issue 9.
Written Opinion, dated Mar. 9, 2011, issued in corresponding Singapore Patent Application No. 201002608-6.
Examination Report, dated Oct. 27, 2011, issued in corresponding Singapore Patent Application No. 201002608-6.
Notice of Reasons for Rejection, dated Dec. 4, 2013, issued in corresponding JP Application No. 2010-530965.
Notice of Reasons for Rejection dated Jul. 8, 2013 issued in corresponding JP Application No. 2010-530965.
Eddy, S. F. et al, Trastuzumab-resistant HER2-driven breast cancer cells are sensitive to epigallocatechin-3 gallate. Cancer Research, Oct. 1, 2007, vol. 67, No. 19, p. 9018-23.
Extended European Search Report issued Aug. 7, 2014 in corresponding European Patent Application No. 08841797.7.
Chisholm et al., "Tamoxifen and epigallocatechin gallate are synergistically cytotoxic to MDA-MB-231 human breast cancer cells", Anticancer Drugs, vol. 15, Issue 9, pp. 889-897, Oct. 2004.
Office Action issued May 1, 2014 in corresponding Korean Patent Application No. 10-2010-7010790.
Lazarus, "Dietary flavonoids may promote health, prevent heart disease", California Agriculture 54(5):33-39. Sep.-Oct. 2000.
Notice of Preliminary Rejection, dated Jun. 2, 2015, issued in corresponding KR patent application No. 10-2015-7005618.
First Examination Report, dated Apr. 21, 2015, issued in corresponding IN patent application No. 2929/DELNP/2010.
Korean Intellectual Property Office, Notice of Preliminary Rejection, issued on Apr. 1, 2015, in KR patent application No. 10-2010-7010790.
Examination Report dated Jul. 7, 2015 issued in corresponding EP Patent Application No. 08841797.7.

* cited by examiner

METHOD OF DELIVERING AN ANTI-CANCER AGENT TO A CELL

CROSS-REFERENCE TO RELATED APPLICATION

This application claims benefit of, and priority from, U.S. provisional patent application No. 60/960,969, filed Oct. 23, 2007, the contents of which are incorporated herein by reference.

FIELD OF THE INVENTION

The present invention relates generally to a method of delivering a bioactive agent to a cell, including a tumour cell in a subject.

BACKGROUND OF THE INVENTION

Flavonoids are one of the most numerous and best-studied groups of plant polyphenols. The flavonoids consist of a large group of low-molecular weight polyphenolic substances naturally occurring in fruits and vegetables, and are an integral part of the human diet. Dried green tea leaves can contain as much as 30% flavonoids by weight, including a high percentage of flavonoids known as catechins (flavan-3-ol derivatives or catechin-based flavonoids), including (−)-epicatechin, (−)-epigallocatechin, (+)-catechin, (−)-epicatechin gallate and (−)-epigallocatechin gallate.

In recent years, these green tea catechins have attracted much attention because they have been recognized to have biological and pharmacological properties, including antibacterial, antineoplastic, anti-thrombotic, vasodilatory, antioxidant, anti-mutagenic, anti-carcinogenic, hypercholesterolemic, antiviral and anti-inflammatory properties, which have been demonstrated in numerous human, animal and in vitro studies (Jankun J., et al. *Nature* 387, 561 (1997); Bodoni A. et al. *J. Nutr. Biochem.* 13, 103-111 (2002); Nakagawa K. et al. *J. Agric. Food Chem.* 47, 3967-3973 (1999)). These biological and pharmacological properties are potentially beneficial in preventing diseases and protecting the stability of the genome.

Many of the beneficial effects of catechins are thought to be linked to the antioxidant actions of the catechins (Terao J., et al. *Arch. Biochem. Biophys.* 308, 278-284 (1994)). Among the catechins, (−)-epigallocatechin gallate (EGCG), which is a major component of green tea, is thought to have the highest activity, possibly due to the trihydroxy B ring and the gallate ester moiety at the C3 position (Isemura M., et al. *Biofactors* 13, 81-85 (2000); Ikeda I., et al. *J. Nutr.* 135, 155 (2005); Lill G., et al. *FEBS Letters* 546, 265-270 (2003); Sakanaka S. and Okada Y. *J. Agric. Food Chem.* 52, 1688-1692 (2004); Yokozawa T., et al., *J. Agric. Food Chem.* 48, 5068-5073 (2000)).

In general, the activity half-life of flavonoids is limited to a few hours inside the body; metabolism of these compounds has not yet been established. Despite the favorable anti-oxidation and anti-cancer properties of the catechins including EGCG, it is impractical to achieve a therapeutic level of this compound in the body by directly ingesting a large amount of green tea, due to the inherent volume constraint. That is, in order to obtain a therapeutic or pharmacological benefit from flavonoids through diet alone, it would be necessary to ingest an amount of food and beverage that is larger than is practical to consume. Moreover, pro-oxidant activity has been reported for several flavonoids including EGCG, making ingesting crude green tea directly a less effective means of delivering EGCG (Yen G. C., et al. *J. Agric. Food Chem.* 45, 30-34 (1997); Yamanaka N., et al. *FEBS Lett.* 401, 230-234 (1997); Roedig-Penman A. and Gordon M. H. *J. Agric. Food Chem.* 1997, 45, 4267-4270).

On the other hand, a relatively high-molecular fraction of extracted plant polyphenols (procyanidins) and synthetically oligomerized (+)-catechin and rutin have been reported to exhibit enhanced physiological properties such as antioxidant and anti-carcinogenic activity compared to low-molecular weight flavonoids, (Zhao J., et al. *Carcinogenesis*, 1999, 20, 1737-1745; Ariga T. and Hamano M. *Agric. Biol. Chem.* 54, 2499-2504 (1990); Chung J. E., et al. *Biomacromolecules* 5, 113-118 (2004); Kurisawa M., et al. *Biomacromolecules* 4, 1394-1399 (2003); Hagerman A. E., et al. *J. Agric. Food Chem.* 46, 1887 (1998)) and without pro-oxidant effects (Hagerman A. E., et al. *J. Agric. Food Chem.* 46, 1887 (1998); Li C. and Xie B. *J. Agric. Food Chem.* 48, 6362 (2000)). However, neither naturally occurring nor synthesized high molecular weight flavonoids are expected to be absorbed and transported to other tissues after ingestion, since these compounds are typically large, form strong complexes with proteins and are resistant to degradation (Zhao J., et al. *Carcinogenesis*, 1999, 20, 1737-1745).

In cases of flavonoids consumed via oral intake of foods and beverages, the flavonoids may play a role as antioxidants to protect the digestive tract from oxidative damage during digestion. However, flavonoids can be expected to remain only in the digestive tract and thus their beneficial physiological activities are not likely to be utilized to other tissues. Moreover, their strong hydrophobicity as well as their tendency to form complexes with proteins makes parenteral delivery of these compounds difficult.

SUMMARY OF THE INVENTION

The present invention provides a method of delivering bioactive anti-cancer agents to a cell, including a tumour cell, using flavonoid conjugates and delivery agents previously described in published International application WO 2006/124000 and published US application 2008/102052.

The present invention is based on the surprising discovery that use of the flavonoid-based delivery agents to deliver anti-cancer agents to a cell results in a synergistic effect between the anti-cancer bioactive agent and the flavonoids. Thus, these conjugates and delivery agents combine the synergistic therapeutic effects arising from the flavonoid portion that acts as a carrier and the bioactive agent that is to be delivered.

In one aspect, there is provided a delivery vehicle comprising an anti-cancer agent and a conjugate of a delivery agent containing a free aldehyde and a flavonoid, having the delivery agent conjugated at the C6 and/or the C8 position of the A ring of the flavonoid.

In another aspect, there is provided a method of delivering an anti-cancer agent to a cell comprising contacting the delivery agent as described herein with the cell.

In another aspect, there is provided a pharmaceutical composition comprising the delivery vehicle as described herein.

In another aspect, there is provided use of the micelle-protein complex as described herein for delivering an anti-cancer agent to a cell in a subject.

Other aspects and features of the present invention will become apparent to those of ordinary skill in the art upon review of the following description, of specific embodiments of the invention in conjunction with the accompanying figures.

BRIEF DESCRIPTION OF THE DRAWINGS

In the figures, which illustrate, by way of example only, embodiments of the present invention.

DETAILED DESCRIPTION

Figure 1:
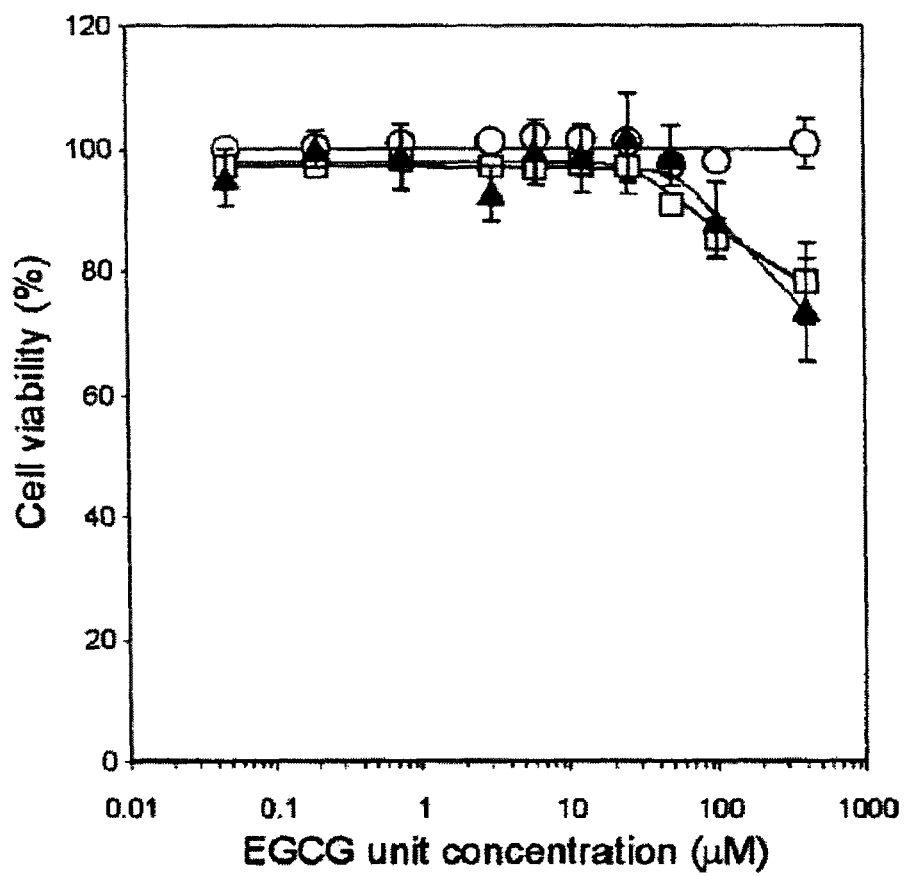
FIG. 1 is a graph depicting cytotoxicity of (□) EGCG, (▲) OEGCG and (○) PEG-EGCG on HMEC. N=5 for samples and N=8 for control.

Flavonoids are known to have a variety of biological properties, including having anti-cancer effects, inhibiting growth of cancer cells. Delivery vehicles comprising flavonoids were previously described in published international application WO 2006/124000 and published US application 2008/102052.

Surprisingly, the inventors have found that the combination of the flavonoid delivery vehicle and bioactive anti-cancer agent has a synergistic anti-cancer effect, greater than the combined effects of each of the flavonoid delivery vehicle and bioactive anti-cancer agent when used alone. Thus, such delivery vehicles loaded with an anti-cancer agent provide an effective way of delivering anti-cancer agents to a cell, taking advantage of the synergistic effect between the anti-cancer activity of the flavonoid portion of the delivery vehicle and the anti-cancer effect of the anti-cancer agent.

The inventors developed a delivery vehicle containing an anti-cancer agent such as a protein, nucleic acid or drug, by self-assembly using flavonoids and conjugates of flavonoids such as EGCG. The delivery vehicles were formed by self-assembly. For example, delivery vehicles were synthesised by (i) two-step self-assembly process involving assembly of oligomeric (−)-epigallocatechin-3-O-gallate (OEGCG) and the anti-cancer agent, and then assembly of the pre-formed OEGCG-anti-cancer agent complex with a conjugate of poly (ethylene glycol) (PEG) and EGCG (PEG-EGCG); and (ii) one-step self-assembly process involving assembly of a conjugate of PEG and OEGCG (PEG-OEGCG) and the anti-cancer agent. Both delivery vehicles formed as stable and highly oriented micellar complexes loaded with the anti-cancer agent via spontaneous self-assembly in a mild aqueous solution. The resulting micellar nanocomplexes characteristically display a PEG outer shell, with an inner core comprised of OEGCG-anti-cancer agent complex.

Since the formation of a micellar nanocomplex is mainly driven by hydrophobic interaction and hydrogen bonding, the delivery vehicles described herein can be used to load a wide variety of anti-cancer agents for improved delivery to a cell.

The delivery vehicles are designed to take advantage of the enhanced permeability and retention (EPR) effect, and to avoid reticuloendothelial system (RES) uptake when administered in vivo, providing for selective accumulation at cancer sites. Ideally, the delivery vehicles preserve the stability of both the flavonoid molecules and the anti-cancer agent from loss of activity and from degradation during delivery, exerting a synergistic therapeutic effect when delivered to a cell. The delivery vehicle may mask the activity of the flavonoid and the anti-cancer agent activity by sequestering these moieties within the inner core of the delivery vehicle until successfully delivered and released at the cell, restoring the respective activities only upon dissociation of the delivery vehicle at the site of a cell.

To demonstrate the synergistic therapeutic effects by the delivery vehicle, the anti-cancer protein Herceptin (trastuzumab) was loaded into the micellar complex, as described in Example 1 below. The micellar complex kept its integrity and showed good stability in the presence of serum without size change as a function of time, and the protein was safely protected from proteolysis within the micellar complex. A greater inhibition was demonstrated with the Herceptin-loaded delivery vehicle as compared to the individual components (OEGCG, PEG-EGCG and Herceptin).

Since the formation of the delivery vehicle is mainly driven by hydrophobic interaction, it can be dissociated by hydrophobic competitors, such as amphiphilic molecules. Thus, the delivery vehicle may be dissociated by bio-amphiphilic molecules (such as plasma membrane lipids) to release the contained therapeutic flavonoid and anti-cancer compounds when the delivery vehicle accumulates at the targeted cell site.

Thus, there is provided a method of delivering an anti-cancer agent to a cell. A delivery vehicle containing a flavonoid and an anti-cancer agent is used, as previously described in published international application WO 2006/124000 and published US application 2008/102052, and as described below. The delivery vehicle is then contacted with the cell to which the anti-cancer agent is to be delivered.

Flavonoid Conjugates and Delivery Vehicles

In order to increase the availability of beneficial flavonoid compounds, the conjugation of flavonoids to various delivery agents through a free aldehyde group on the delivery agent to the A ring of the flavonoid allows for modification of the physical properties of the flavonoid without disrupting the polyphenol structure of the flavonoid, while augmenting the biological and pharmacological properties of the flavonoid.

That is, the aldehyde-mediated conjugation of a delivery agent to the flavonoid results in attachment of the delivery agent at the C6 and/or C8 position of the flavonoid A ring, and does not disrupt or affect the B and C rings of the flavonoid or the various hydroxyl groups on the flavonoid.

Conjugation of a delivery agent to a flavonoid can provide a composition that is suitable for administration to a subject by incorporating the flavonoid into a particular vehicle formed with the delivery agent, and can allow for administration of higher concentrations of flavonoids than can be obtained through diet. The delivery agent can provide stability to the composition, resulting in a composition that is metabolized or degraded more slowly, and which thus may have a longer half-life in the body than the unconjugated flavonoid alone. For example, the delivery agent may be of such a nature that the flavonoid is incorporated into a composition that enhances the water-solubility of the flavonoid, which can avoid uptake by the reticuloendothelial system and subsequent clearance by the kidneys, resulting in a longer half-life in the body. Conjugation of other delivery agents may protect the flavonoid from enzyme degradation.

A delivery agent may be conjugated to a flavonoid by reacting the delivery agent with the flavonoid in the presence of an acid catalyst, the delivery agent having a free aldehyde group, or a group that is able to be converted to a free aldehyde group in the presence of acid.

The flavonoid may be any flavonoid from the general class of molecules derived from a core phenylbenzyl pyrone structure, and includes flavones, isoflavones, flavonols, flavanones, flavan-3-ols, catechins, anthocyanidins and chalcones. In a particular embodiment the flavonoid is a catechin or a catechin-based flavonoid. A catechin, or a catechin-based flavonoid is any flavonoid that belongs to the class generally known as catechins (or flavan-3-ol derivatives), and includes catechin and catechin derivatives, including epicatechin, epigallocatechin, catechin, epicatechin gallate and epigallocatechin gallate, and including all possible stereoisomers of catechins or catechin-based flavonoids. In particular embodiments, the catechin-based flavonoid is (+)-catechin or (−)-epigallocatechin gallate. (−)-epigallocatechin gallate (EGCG) is thought to have the highest activity among the catechin-based flavonoids, possibly due to the trihydroxy B ring and gallate ester moiety at the C3 position of this flavonoid.

The delivery agent is any chemical group or moiety that contains a free aldehyde or group, or a functional group that can be converted to a free aldehyde group in the presence of acid, for example an acetal group. The delivery agent is capable of being formed into a delivery vehicle, thus allowing for the incorporation of a conjugated flavonoid into the delivery vehicle without compromising the biological or pharmacological properties of the flavonoid. As well, the delivery agent should be biocompatible, and may be biodegradable in some embodiments.

The following discussion refers to an embodiment in which the flavonoid is a catechin-based flavonoid and in which the delivery agent is a polymer. However, it will be understood that the aldehyde condensation reaction between an aldehyde-containing chemical group and a flavonoid is applicable to conjugation of any delivery agent having a free aldehyde group, including following acid treatment of the delivery agent, to any flavonoid, as described above.

Thus, the reaction may involve conjugation of a polymer containing a free aldehyde group or a group that is able to be converted to a free aldehyde group in the presence of acid to a catechin-based flavonoid.

The catechin-based flavonoid may be a single monomeric unit of a catechin-based flavonoid or it may be an oligomer of one or more catechin-based flavonoids. As stated above, conjugation of a polymer to a flavonoid results in augmentation of the flavonoid's biological or pharmacological properties. As well, an oligomer of the catechin-based flavonoid tends to have amplified or augmented levels of the biological and pharmacological properties associated with catechin-based flavonoids, and may even have reduced pro-oxidant effects that are sometimes associated with monomeric catechin-based flavonoids. Thus, the catechin-based flavonoid is an oligomerized catechin-based flavonoid having amplified or augmented flavonoid properties.

Oligomers of catechin-based flavonoids are known, including oligomers prepared through enzyme-catalyzed oxidative coupling and through aldehyde-mediated oligomerization. An aldehyde-mediated oligomerization process results in an unbranched oligomer that has defined linkages, for example through carbon-carbon linkages such as $CH-CH_3$ bridges linked from the C6 or C8 position on the A ring of one monomer to the C6 or C8 position on the A ring of the next monomer, including in either possible stereoconfiguration, where applicable. Thus, the $CH-CH_3$ linkage may between the C6 position of the A ring of one monomer and either of the C6 or C8 position of the next monomer or it may be between the C8 position of the A ring of the first monomer and either of the C6 or C8 position of the next monomer.

The oligomer of the catechin-based flavonoid may be of 2 or more monomeric units linked together. In certain embodiments, the catechin-based flavonoid oligomer has from 2 to 100 flavonoid monomer units, from 10 to 100, from 2 to 80, from 10 to 80, from 2 to 50, from 10 to 50, from 2 to 30, from 10 to 30, from 20 to 100, from 30 to 100 or from 50 to 100 monomeric units.

The polymer may be any polymer having a free aldehyde group prior to conjugation with the catechin-based flavonoid, or having a group that is converted to an aldehyde group in the presence of acid, for example an acetal group. Furthermore, it will be understood that the polymer should be non-toxic, biocompatible and suitable for pharmacological use. The polymer may also have other desirable properties, for example, the polymer may have low immunogenicity, and it may be biodegradable or non-biodegradable depending on the desired biological application of the composition, for example, for controlled release of catechin-based flavonoids and the anti-cancer agent at a particular site in a body.

The polymer may be chosen based on its particular characteristics and its ability to form certain types of delivery vehicles. For example, the polymer may be an aldehyde-terminated poly(ethylene glycol), or it may be hyaluronic acid derivatized with an aldehyde group, or a derivative of such polymers. Alternatively, the polymer may be a phenoxymethyl(methylhydrazono) dendrimer (PMMH), for example, cyclotriphosphazene core PMMH or thiophosphoryl core PMMH. The polymer may also be any biological polymer, modified to contain a free aldehyde group or a group that is convertible to an aldehyde in the presence of acid, for example an aldehyde-modified protein, peptide, polysaccharide or nucleic acid. In one particular embodiment the polymer is an aldehyde-terminated poly(ethylene glycol) (PEG-CHO). In another particular embodiment, the polymer is aldehyde-derivatized hyaluronic acid, hyaluronic acid conjugated with aminoacetylaldehyde diethylacetal, or either of the aforementioned hyaluronic acid polymers derivatized with tyramine.

The free aldehyde group on the polymer allows for the conjugation of the polymer in a controlled manner to either the C6 or the C8 position of the A ring, or both, of the flavonoid structure, thus preventing disruption of the flavonoid structure, particularly the B and C rings of the flavonoid, and thus preserving the beneficial biological and pharmacological properties of the flavonoid.

The polymer is conjugated to the catechin-based flavonoid via a reaction of the aldehyde group of the polymer with the C6 and/or the C8 position of the A ring of the catechin-based flavonoid.

The conjugate is synthesized using acid catalysis of a condensation of the aldehyde group of the polymer with the catechin-based flavonoid, or using acid to convert a functional group on the polymer to a free aldehyde prior to condensation of the aldehyde group with the catechin-based flavonoid.

To conjugate the polymer and the catechin-based flavonoid, the polymer and the catechin-based flavonoid may be separately dissolved in a suitable solvent. The polymer with the free aldehyde is added, for example by dropwise addition, to the solution containing the catechin-based flavonoid, in the presence of an acid. The reaction is allowed to go to completion. Following the conjugation reaction, excess unreacted polymer or catechin-based flavonoid can be removed from the conjugated composition, for example by dialysis or by molecular sieving.

The ratio of catechin-based flavonoid to polymer may be varied, so that there is only one polymer moiety attached to the catechin-based flavonoid portion of the polymer, or so that there is a catechin-based flavonoid portion attached at more than one position on the polymer, or so that the catechin-based flavonoid portion has two polymer portions attached, one at either of the C6 and C8 positions of the catechin-based flavonoid.

The ratio of polymer to catechin-based flavonoid in the final composition can be controlled through the ratio of starting reagents. For example, when the molar ratio of polymer moiety to catechin-based flavonoid moiety is about 1, a single polymer moiety will be attached to a single catechin-based flavonoid moiety (either monomeric or oligomeric may be used). However, at higher concentrations of polymer, for example at a 10:1 molar ratio of polymer to catechin-based flavonoid, a composition having a tri-block structure of polymer-flavonoid-polymer may be obtained.

A conjugate of a polymer containing a free aldehyde and a catechin-based flavonoid, having the polymer conjugated at the C6 and/or the C8 position of the A ring of the flavonoid is also contemplated.

Conjugation of the polymer also allows for the incorporation of catechin-based flavonoids into various compositions or vehicles. By selection of the particular polymer containing a free aldehyde group based on the physical properties of the polymer, it is possible to incorporate flavonoids into a variety of different vehicle types, allowing for the delivery of high concentrations of flavonoids in different contexts to various targeted areas of the body.

Thus, the conjugate resulting from the above-described reaction may be formed into a delivery vehicle, depending on the nature of the polymer portion of the conjugate. The delivery vehicle may be used to deliver the catechin-based flavonoid to a body, including a particular targeted site in a body, depending on the nature of the delivery vehicle.

Anti-Cancer Agents

An anti-cancer agent is included in the delivery vehicle, which is then contacted with a cell to which the anti-cancer agent is to be delivered. Thus, there is provided a delivery vehicle comprising a catechin-based flavonoid conjugated to a polymer through a free aldehyde group on the polymer, the delivery vehicle further comprising an anti-cancer agent.

The anti-cancer agent may be any agent that has an anti-cancer effect on a cell, including an anti-tumour effect, such as a cytotoxic, apoptotic, anti-mitotic anti-angiogenesis or inhibition of metastasis effect. The anti-cancer effect is intended to include inhibition or reduction of tumour cell growth, inhibition, or reduction of carcinogenesis, killing of tumour cells, or inhibition or reduction of carcinogenic or tumourogenic properties of a cell, including a tumour cell.

An anti-cancer agent includes a protein, a nucleic acid, a small molecule or a drug. An anti-cancer agent that is a protein may be a peptide, an antibody, a hormone, an enzyme, a growth factor, or a cytokine. An anti-cancer agent that is a nucleic acid may be single stranded or double stranded DNA or RNA, a short hairpin RNA, an siRNA, or may comprise a gene encoding an anti-cancer product. Also included in the scope of anti-cancer agent is a chemotherapeutic agent or an angiogenesis inhibitor. The anti-cancer agent may be an antibody, including a monoclonal antibody; directed against a tumour cell-surface marker, an immunoregulatory peptide, a cytokine or a growth factor. The anti-cancer agent may be Herceptin (trastuzumab) or TNP470.

Formation of Delivery Vehicle Containing Anti-Cancer Agent

In one particular embodiment, the delivery vehicle is a micellar nanocomplex, which is suitable for parenteral delivery of a catechin-based flavonoid and an anti-cancer agent to a cell, including a cell located at a particular site within a body of a subject.

To form the delivery vehicle containing the anti-cancer agent, the polymer is chosen to have properties that allow it to assemble with the catechin-based flavonoid portion of the composition, protecting the flavonoid from the solution environment. If a suitable solvent is chosen in which the polymer portion of the conjugate is soluble and is more soluble than the catechin-based flavonoid, the conjugate will self-assemble, excluding the solution from the flavonoid core, thus allowing for assembly of micellar complexes.

In a particular embodiment of the micellar nanocomplex delivery vehicle, the polymer chosen is aldehyde-terminated PEG, or a derivative thereof. PEG is a polymer widely used as a pharmacological ingredient, and possesses good hydrophilic, non-toxic, non-immunogenic and biocompatibility characteristics with low biodegradability.

By conjugating PEG-CHO to a catechin-based flavonoid, a conjugate is formed that has strong self-assembly tendencies. In one embodiment, PEG is conjugated to a monomer of a catechin-based flavonoid, to form a PEG-flavonoid. The delivery vehicle is formed together with non-conjugated catechin-based flavonoids and the anti-cancer agent. Thus, the central core contains relatively high concentrations of a flavonoid and the anti-cancer agent, while the external shell of the micellar nanocomplex comprises the conjugated PEG-monomeric flavonoid, and is assembled in a two-step process. In a particular embodiment, the central core is oligomeric EGCG (OEGCG) and the external core is made up of conjugated PEG-EGCG.

Formation of this two-step assembly of the delivery vehicle results in temporary partial or complete masking of the biological activities of the oligomeric flavonoid that is incorporated into the core of the delivery vehicle, as well as protecting the anti-cancer agent from degradation prior to delivery to the cell. For example, while assembled into core of the delivery vehicle, the augmented properties of the oligomerized EGCG are less available, due to physical interactions with other molecules in the assembled core portion of the delivery vehicle. Upon release from the delivery vehicle, for example by fusion of the vehicle with a cellular phospholipid membrane, the components of the delivery dissociate, unmasking the biological properties of the oligomeric catechin-based flavonoid, and releasing the anti-cancer agent for delivery into the cell.

This embodiment of the delivery vehicle is well suited to deliver the anti-cancer agent. Since the catechin-based flavonoids have a rigid, multi-ring core structure, these molecules associate well with anti-cancer agents such as proteins and nucleic acids, as well as other molecules containing ring structures, likely by stacking of the catechin rings with the ring or rings on the anti-cancer agent. Thus, an oligomeric catechin-based flavonoid can be used to associate with the anti-cancer agent prior to assembly in the micellar nanocomplex.

The concentration of the anti-cancer agent is chosen depending on the total amount of anti-cancer agent that is to be delivered to a particular site in a body, and on the amount of anti-cancer agent that can be included in the micellar nanocomplex without destabilizing the micellar structure. In certain embodiments, the anti-cancer agent may constitute up to 50%, or up to 40%, w/w of the micellar complex.

The biological activity of the anti-cancer agent is also temporarily partially or completely masked while incorporated into the present delivery vehicles. As with the oligomeric catechin-based flavonoid, the biological properties of the anti-cancer agent are masked or sequestered, making them less available while the anti-cancer agent is assembled in the delivery vehicle, meaning that the anti-cancer agent is not able to exert anti-cancer activity or interact with other molecules in a bioactive manner while contained in the delivery vehicle, and is also protected from activity of other molecules. Upon release of the anti-cancer agent from the delivery vehicle, the biological properties of the anti-cancer agent are once again available, and the anti-cancer agent is able to exert an anti-cancer effect once delivered to the cell.

In another embodiment, PEG is conjugated to an oligomeric catechin-based flavonoid. This embodiment of the delivery agent has strong self-assembly properties and can be self-assembled in a single step process. As with the two-step assembly micellar nanocomplex above, the single-step assembling micellar nanocomplex includes the anti-cancer agent.

The above micellar nanocomplexes are of nanoscale dimensions, and may be from about 1 nm to about 10000 nm in diameter, or from about 20 nm to about 4000 nm in diameter, or from about 20 nm to about 100 nm in diameter. The size of the micellar nanocomplexes can be varied by varying the length of the oligomerized catechin-based flavonoid, the length of the polymer, and the concentration of unconjugated oligomerized catechin-based flavonoid. The size of the micellar nanocomplex may be pH dependent, depending on the polymer used. For example, in micellar nanocomplexes in which the conjugated polymer is PEG, the diameter of the micelles tends to decrease with increasing pH.

Generally, the micellar nanocomplexes containing the anti-cancer agent undergo self assembly and thus little synthesis is required. For the two step process, the components that are to form the core, including the anti-cancer agent, are dissolved in a suitable solvent, for example in diluted DMSO or methanol, and are allowed to assemble. The solvent is a solvent in which the core components are soluble, and which may be miscible in water, or which may be volatile, or from which the assembled micelles can otherwise be isolated or extracted. As indicated above, the core components include an anti-cancer agent and a catechin-based flavonoid, for example an oligomeric catechin-based flavonoid. The polymer-catechin-based flavonoid conjugate that is to form the outer shell is then added to the solution and the micellar complex is allowed to form.

For the one step self-assembly process, the polymer-catechin-based flavonoid conjugate together with the anti-cancer agent, is dissolved in a suitable buffer as described for the two-step process and the micellar nanocomplex is allowed to assemble.

This micellar nanocomplex system provides the ability to achieve controlled biodistribution of catechin-based flavonoids and prolonged circulation half-life in bloodstream due to the PEG outer shell, as well as amplified pathological activities of the catechin-based flavonoid compound, with the added benefit that such compounds may be accompanied by therapeutic effect of the anti-cancer agent loaded in the inner core of the micelle. Where the anti-cancer agent is a sensitive molecule such as a protein, the nanoscale micelles offer a convenient delivery vehicle with the advantage of a gentle, self-assembly method that does not involve the mechanical, thermal and chemical stresses that can be associated with conventional encapsulation techniques currently used, which conventional techniques may lead to denaturation of sensitive bioactive anti-cancer agents such as proteins.

In another particular embodiment, the delivery vehicle is a hydrogel, which can be used as a dressing, for sustained release delivery of an anti-cancer agent, or as a support for tissue regeneration.

The polymer is chosen to have good swellability characteristics and to have appropriate groups available for cross-linking of the polymer moieties, and to be non-toxic and biocompatible, and in some embodiments to be biodegradable.

In a particular embodiment of the hydrogel, the polymer, is aldehyde derivatized hyaluronic acid, or a derivative of hyaluronic acid such as hyaluronic acid aminoacetylaldehyde diethylacetal conjugate, or a tyramine derivative of aldehyde-derivatized hyaluronic acid or hyaluronic acid aminoacetylaldehyde diethylacetal conjugate.

Conjugates comprising a hyaluronic acid-catechin-based flavonoid can be readily cross-linked to form a hydrogel, without disruption of the biological or pharmacological properties of the flavonoid. Such hydrogels also comprise an anti-cancer agent as described above, for release of the anti-cancer agent to a cell at the site where the hydrogel is applied.

The hyaluronic acid-flavonoid conjugate is synthesized by reacting the hyaluronic acid with the catechin-based flavonoid under acidic conditions, for example from about 1 to about 5, or for example at pH of about 1. The conjugated polymer-flavonoid is then purified, for example by dialysis, and then mixed with the anti-cancer agent, and a cross-linking agent, such as hydrogen peroxide. A cross-linking catalyst is added, for example horseradish peroxidase, and the hydrogel may then be quickly poured in to a mold to form a desired shape before the cross-linking reaction is completed. For example, the hydrogel may be formed into a slab suitable for application as a wound dressing.

The components of the hydrogel may also be injected and reacted to form the hydrogel in vivo, for example by injecting an uncrosslinked conjugate together with an anti-cancer agent, together with a cross-linking agent, such as hydrogen peroxide and a cross-linking catalyst, for example, horseradish peroxidase. Such a hydrogel is useful for drug delivery to a specific site in a body, or for tissue engineering.

Since hyaluronic acid has multiple sites that may react with the flavonoid during the conjugation reaction, by varying the concentration of the catechin-based flavonoid in the starting reaction, it is possible to vary the degree of conjugation between the hyaluronic acid polymer and the catechin-based flavonoid. For example, the ratio of reactants may be adjusted so that the resulting conjugate has from about 1% to about 10% of the sites on the polymer conjugated with the flavonoid. Alternatively, additional hyaluronic acid that has not been conjugated can be added to the mixture prior to cross-linking of the hydrogel so that some of the polymer molecules in the hydrogel will not be conjugated to the flavonoid.

Delivery of Anti-Cancer Agent to a Cell

In order to deliver the anti-cancer agent to a cell using the flavonoid-containing delivery vehicle, the delivery vehicle comprising the anti-cancer agent is contacted with a cell, which may allow for uptake of the anti-cancer agent into the cell.

Thus, delivery of the anti-cancer agent to a cell comprises contacting the delivery vehicle containing the anti-cancer agent with the surface of a cell. Without being limited to any particular theory, the delivery system is dissociated by amphiphilic molecules such as lipids of plasma membranes, and thus the anti-cancer agent is released at the site of the cell by passive targeting, and may be released into the cell.

The cell to which the anti-cancer agent is to be delivered may be any cell, including an in vitro cell, a cell in culture, or an in vivo cell within a subject. The term "cell" as used herein refers to and includes a single cell, a plurality of cells or a population of cells where context permits, unless otherwise specified. The cell may be an in vitro cell including a cell explanted from a subject or it may be an in vivo cell in a subject. Similarly, reference to "cells" also includes reference to a single cell where context permits, unless otherwise specified.

The cell may be derived from any organism, for example an animal including a mammal including a human.

When delivered to the cell, the anti-cancer agent retains its anti-cancer function, as described above, and may be delivered in to the cell. A skilled person can readily determine whether the anti-cancer agent has been delivered into the cell using known methods and techniques, including protein detection methods, immunoassays and fluorescence labelling techniques.

The above described compositions and delivery vehicles are well-suited for controlled and targeted delivery of anti-cancer agents together with catechin-based flavonoids to particular sites within the body of a subject. The flavonoids can provide antibacterial, antineoplastic, anti-thrombotic, vasodilatory, antioxidant, anti-mutagenic, anti-carcinogenic, hypercholesterolemic, antiviral and anti-inflammatory activity at the targeted site. In addition, the delivery vehicles include an anti-cancer agent, making the delivery vehicles useful in the treatment of cancer. For example, immunoregulatory peptides and proteins including cytokines and growth factors have emerged as an important class of drugs for the treatment of cancer.

Thus, there is presently provided a method of delivering anti-cancer agent to a subject comprising administering a delivery vehicle comprising conjugate of a polymer containing a free aldehyde and a catechin-based flavonoid, having the polymer conjugated at the C6 and/or the C8 position of the A ring of the flavonoid is also contemplated, as described above. In certain embodiments, the conjugate is formed into a delivery vehicle, such as a micellar nanocomplex or a hydrogel, as described above.

The subject is any animal, including a human, in need of treatment with an anti-cancer agent.

Therefore, there is provided a pharmaceutical composition comprising a delivery vehicle containing the anti-cancer agent and flavonoid as described above. The pharmaceutical composition may further include a pharmaceutically acceptable diluent or carrier. The pharmaceutical composition may routinely contain pharmaceutically acceptable concentration of salts, buffering agents, preservatives and various compatible carriers. For all forms of delivery, the delivery vehicle may be formulated in a physiological salt solution.

The proportion and identity of the pharmaceutically acceptable diluent or carrier is determined by the chosen route of administration, compatibility with biologically active proteins if appropriate, and standard pharmaceutical practice.

The pharmaceutical composition can be prepared by known methods for the preparation of pharmaceutically acceptable compositions suitable for administration to subjects, such that an effective amount of the delivery vehicle and any additional active substance or substances is combined in a mixture with a pharmaceutically acceptable vehicle. An effective amount of delivery vehicle is administered to the subject. The term "effective amount" as used herein means an amount effective, at dosages and for periods of time necessary to achieve the desired result, for example to deliver the anti-cancer agent to the target cell or cell population within the subject, including a desired amount of the anti-cancer agent to the cell based on factors including the effect of the anti-cancer agent, the effect of the flavonoid and the synergistic effect of the anti-cancer agent and the flavonoid together.

Suitable vehicles are described, for example, in Remington's Pharmaceutical Sciences (Remington's Pharmaceutical Sciences, Mack Publishing Company, Easton, Pa., USA 1985). On this basis, the compositions include, albeit not exclusively, solutions of the delivery vehicle, in association with one or more pharmaceutically acceptable vehicles or diluents, and contained in buffer solutions with a suitable pH and iso-osmotic with physiological fluids.

Under ordinary conditions of storage and use, such pharmaceutical compositions may contain a preservative to prevent the growth of microorganisms, and that will maintain any biological activity of the anti-cancer agent. A person skilled in the art would know how to prepare suitable formulations. Conventional procedures and ingredients for the selection and preparation of suitable formulations are described, for example, in Remington's Pharmaceutical Sciences and in The United States Pharmacopeia: The National Formulary (USP 24 NF19) published in 1999. Alternatively, the delivery vehicle may be formulated at a time sufficiently close to use by mixing the components, without the need for preservatives.

The delivery vehicle may be administered using known methods, which will depend on the form of the delivery vehicle. Non-oral routes are preferred. If the delivery vehicle is formulated as a solution, or in the form of micellar nanoparticles, the delivery vehicle may be delivered parenterally, including intravenously, intramuscularly, or by direct injection into a targeted tissue or organ. If the delivery vehicle is formulated as a hydrogel, the conjugate may be applied topically or by surgical insertion at a wound site.

When administered to a subject, the delivery vehicle is administered in an amount effective and at the dosages and for sufficient time period to achieve a desired result. For example, the delivery vehicle may be administered in quantities and dosages necessary to deliver an anti-cancer agent which may function to alleviate, improve, mitigate, ameliorate, stabilize, prevent the spread of, slow or delay the progression of or cure a disease or disorder, or to inhibit, reduce or impair the activity of a disease-related enzyme. A disease-related enzyme is an enzyme involved in a metabolic or biochemical pathway, which when the pathway is interrupted, or when regulatory control of the enzyme or pathway is interrupted or inhibited, the activity of the enzyme is involved in the onset or progression of a disease or disorder, for example, cancer.

The effective amount of delivery vehicle to be administered to a subject can vary depending on many factors such as the pharmacodynamic properties of the delivery vehicle, including the anti-cancer agent, the polymer moiety and the catechin-based flavonoid moiety, the mode of administration, the age, health and weight of the subject, the nature and extent of the disorder or disease state, the frequency of the treatment and the type of concurrent treatment, if any, and the concentration and form of the delivery vehicle.

One of skill in the art can determine the appropriate amount based on the above factors. The delivery vehicle may be administered initially in a suitable amount that may be adjusted as required, depending on the clinical response of the subject. The effective amount of delivery vehicle can be determined empirically and depends on the maximal amount of the delivery vehicle that can be administered safely. However, the amount of delivery vehicle administered should be the minimal amount that produces the desired result.

There is also provided a delivery vehicle as described above containing the anti-cancer agent and flavonoid.

There is also provided use of the above-described delivery vehicle for delivering the anti-cancer agent to a cell, or use of the above-described delivery vehicle for the manufacture of a medicament for delivering the anti-cancer agent to a cell, including when the cell is an in vivo cell in a subject.

The invention is further illustrated by the following non-limiting example.

EXAMPLE

Example 1

Synergistic Therapeutic Effects of Protein-Loaded Micellar Complex Composed of Green Tea Derivatives Materials and Methods Synthesis of OEGCG and PEG-EGCG: OEGCG was synthesized by the Baeyer reaction of EGCG (Kurita Ltd.) and acetaldehyde (pH 2). To synthesize PEG-EGCG, the aldehyde-terminated PEG (Mw 5000, NOF Co.) and EGCG were reacted at pH=2.

The micellar complexes were formed as previously described in published international application WO 2006/124000 and published US application 2008/102052.

Cytotoxicity Test: Cytotoxicity of EGCG derivatives was examined with human normal mammary epithelial cells (HMEC, Cambrex, USA), and compared to that of intact EGCG. Cells were plated ($1 \times 10^4$ cells in mammary epithelial growth medium/well) in quintuplicate and octuplicate for samples and control, respectively, in 96-well microplates, and allowed to adhere overnight. After the cells were treated with different concentrations of EGCG, OEGCG or PEG-EGCG for 2 days, the cell viability was estimated using Alamar Blue, a dye that would be reduced by the cytochrome c activity of cells.

Proteolysis Assessment: Protein degradation was determined by monitoring the fluorescence intensity increment in FITC-BSA when samples were subjected to proteinase K (0.05 mg/ml), using a fluorescence spectrophotometer (Hitachi, Japan, $\lambda_{ex}$=490 nm and $\lambda_{em}$=530 nm). All measurements were run in triplicate.

Cancer Cell Proliferation Assessment: SKBR-3 cells (ATCC, HTB3O, USA) were plated ($1 \times 10^4$ cells in McCoy's 5 A medium/well) in quintuplicate and octuplicate for samples and control, respectively, in 96-well microplates and allowed to adhere overnight. The culture media were then replaced by media containing the samples (OEGCG, PEG-EGCG, Herceptin (0.5 mg/ml), Herceptin-loaded micellar complex, and BSA-loaded micellar complex), and the cells were incubated at 37° C. in 5% of $CO_2$. At the time points indicated, the culture media were replaced by the phenol red-free media containing 10% of Alamar Blue. Cell proliferation was determined from the reduction in dye absorbance at 570 and 600 nm after 4 h of incubation.

Results

The micellar complexes were synthesised by (i) two-step self-assembly process involving assembly of oligomeric (−)-epigallocatechin-3-O-gallate (OEGCG), including with the relevant protein (fluorescent marker protein or anti-cancer agent) where applicable, and then assembly of the pre-formed OEGCG (plus protein) complex with a conjugate of poly (ethylene glycol) (PEG) and EGCG (PEG-EGCG); or (ii) one-step self-assembly process involving assembly of a conjugate of PEG and OEGCG (PEG-OEGCG) (and the relevant protein where applicable). In both instances, the micellar complexes immediately formed as stable and highly oriented micellar complexes, including loaded with the relevant protein, via spontaneous self-assembly in a mild aqueous solution and displayed a PEG outer shell with an inner core comprised of OEGCG (plus protein) complex.

Figure 2:
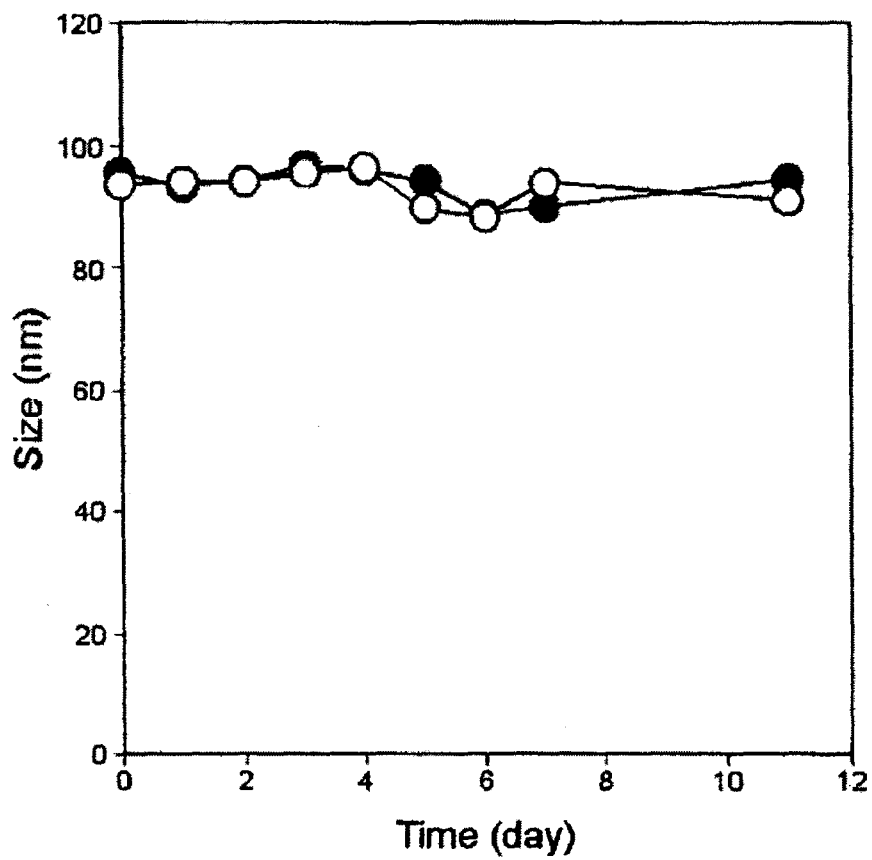
FIG. 2 is a graph depicting the size of the micellar complex in the (○) absence and (●) presence of serum. N=3.

The PEG-EGCG showed no cytotoxicity, while the OEGCG and EGCG displayed low cytotoxicity for HMEC (see FIG. 1). The micellar complex kept its integrity, and demonstrated good stability in the presence of serum without size change (see FIG. 2).

Figure 3:
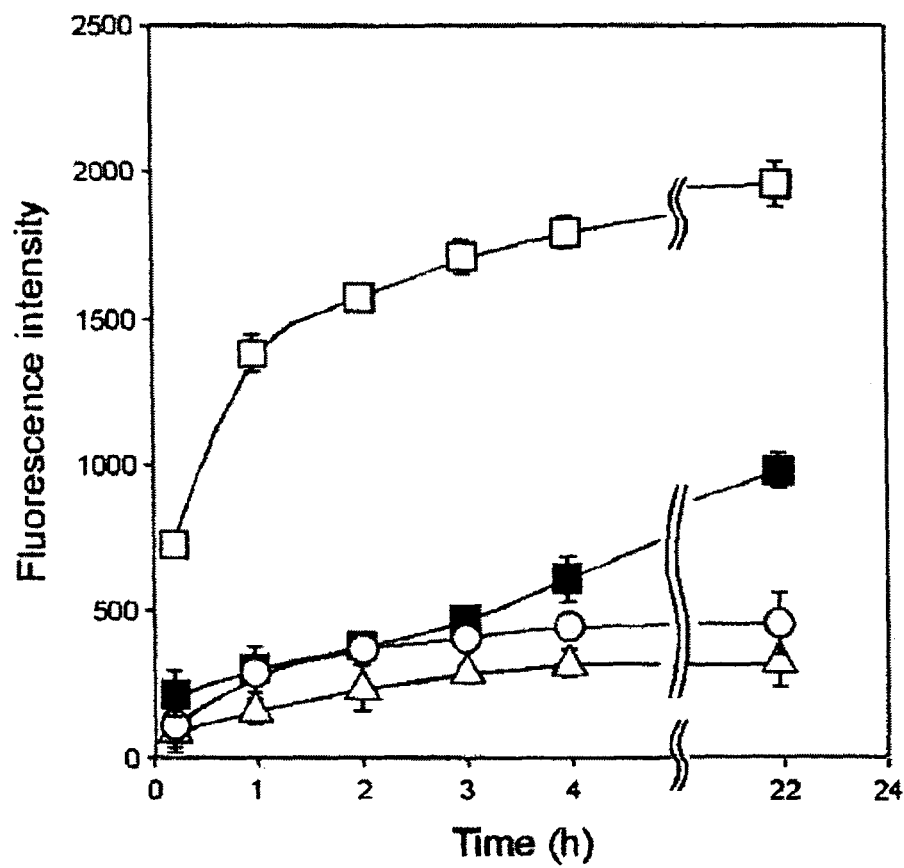
FIG. 3 is a graph depicting the fluorescene intensity of (□) free FITC-BSA, (○) FITC-BSA and OEGCG complex, (Δ) (FITC-BSA+OEGCG) in PEG-EGCG complex in the presence of proteinase K; and (■) free FITC-BSA in the absence of proteinase K. N=3.

The micellar complex was loaded with a fluorescence-labeled protein (FITC-BSA) and subjected to a protease (proteinase K) to investigate protein degradation over time (FIG. 3). The fluorescence intensity of free FITC-BSA greatly increased with time, indicating protein degradation by proteinase K. In contrast, the fluorescence intensity of FITC-BSA loaded in the micellar complexes was kept very low (even lower than that of free FITC-BSA in the absence of proteinase K), illustrating that the protein was robustly protected from proteolysis in these systems.

Figure 4:
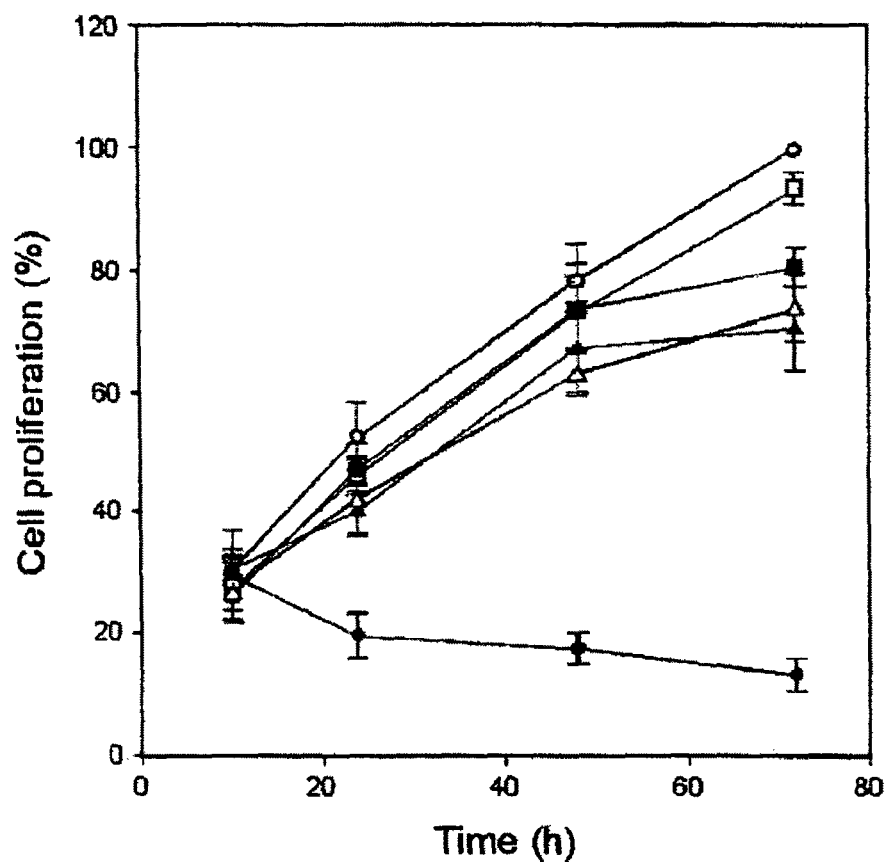
FIG. 4 is a graph depicting in vitro cell proliferation of SKBR-3 cells in the presence of (□) PEG-EGCG, (■) OEGCG, (Δ) Herceptin, (●) (Herceptin+OEGCG) in PEG-EGCG complex, (▲) (BSA+OEGCG) in PEG-EGCG complex, and (○) control (untreated cells). N=5 for samples and N=8 for control.
Figure 5:
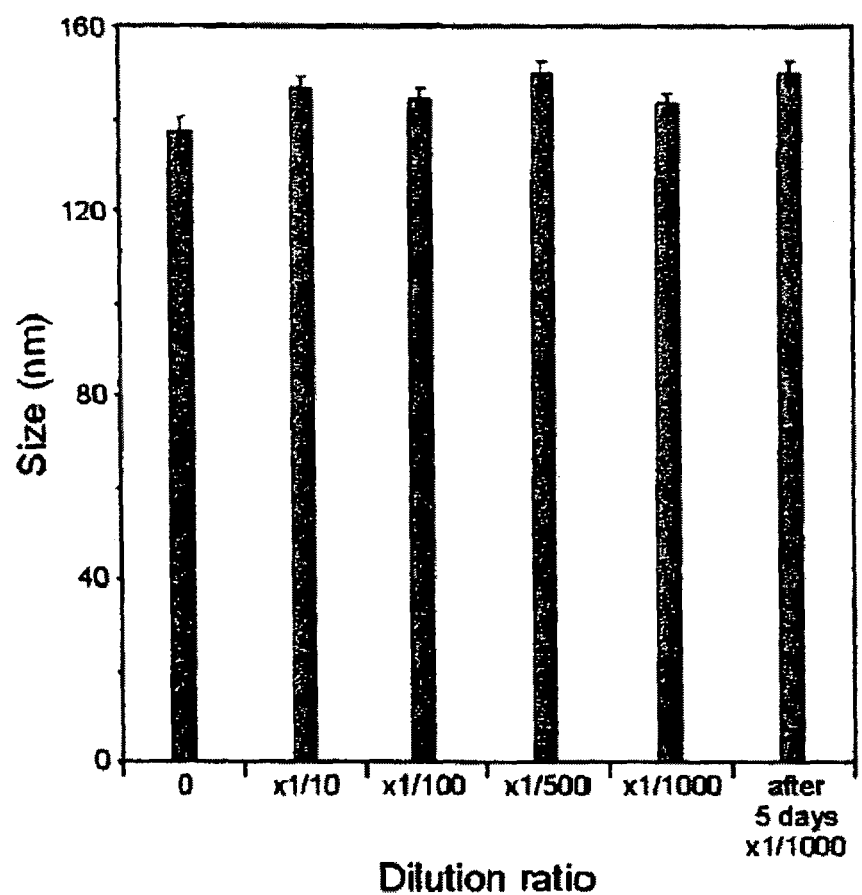
FIG. 5 is a graph depicting the size of the (Herceptin+OEGCG) in PEG-EGCG complex subjected to suspension dilution. N=3.

The inhibition of cancer cell growth was explored in vitro for the micellar complex loaded with Herceptin (trastuzumab), which is a humanized monoclonal antibody against the HER2/neu (erbB2) receptor that induces regression of HER2-overexpressing metastatic breast cancer tumors (FIG. 4). The Herceptin-loaded micellar complex showed no size reduction, tested up to a thousand-fold dilution (FIG. 5). When SKBR-3 (HER2-overexpressing human breast cancer cell line) was treated with either free Herceptin or the carrier components (OEGCG or PEG-EGCG), cell growth was observed to be inhibited. The micellar complex loaded with BSA showed more inhibition effect than OEGCG or PEG-EGCG alone (whereas BSA itself showed no effect). Notably, the Herceptin-loaded micellar complex showed an impressively greater inhibition effect, as compared to the individual components delivered (OEGCG, PEG-EGCG or Herceptin) and the BSA-loaded micellar complex.

Figure 6:
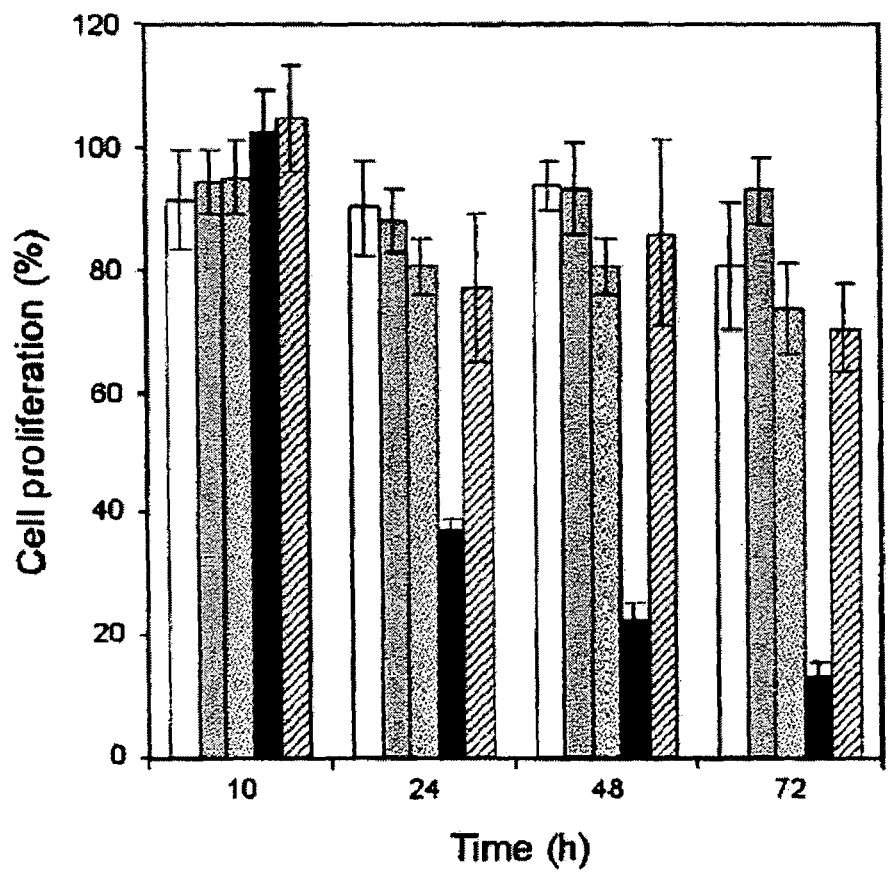
FIG. 6 is a graph depicting in vitro proliferation of SKBR-3 cells in the presence of OEGCG, PEG-EGCG, Herceptin, (Herceptin+OEGCG) in PEG-EGCG complex, and (BSA+OEGCG) in PEG-EGCG complex (bars from left to right in each group). Percentage of cell proliferation was normalized with the control at each time point. N=5 for samples and N=8 for control.

Since the formation of micellar nanocomplex is mainly driven by hydrophobic interaction, the complex would dissociate by hydrophobic competition of the surfactants. The complex could gradually dissociate and release components by interaction with bio-amphiphilic molecules, such as lipids of cell membrane, while the complex was retained with the cells. The micellar complex showed a time lag before exhibiting the therapeutic effect (FIG. 6), i.e. no effect was displayed at early time points (e.g. at 10 h), whereas the free protein and the individual carrier components started to exert anticancer effects immediately. This illustrated the structural advantage of the micellar complex, which was loaded with protein within a PEG outer shell. Besides the delayed release, the micellar complex provided for sustained release of the therapeutic molecules (proteins and carrier components) by dissociation resulting from interaction with cells. These features would be particularly useful and advantageous in light of the fact that the carrier would need to travel from the point of administration to the intended target sites before exerting the therapeutic activities.

Discussion

A core-shell micellar nanocomplex carrier has been synthesized with two EGCG derivatives that were designed to bind with proteins in a spatially ordered structure. These complexes formed micellar nanocomplexes through spontaneous self-assembly in an aqueous solution (FIG. 1). The micellar nanocomplexes were derived by two self-assembly processes: (i) via the complexation between oligomerized EGCG (OEGCG) and proteins to form the core, and (ii) via the complexation of poly(ethylene glycol)-EGCG (PEG-EGCG) surrounding the pre-formed core to form the shell. The resulting micellar nanocomplex displayed a PEG shell with a core of OEGCG-protein complex. This structural feature can serve to reduce protein immunogenicity and prevent rapid renal clearance and proteolysis of protein by reticuloendothelial system uptake, decreasing the need for frequent injections or infusion therapy. The highly water-soluble shell of PEG and the tailored size (<100 nm) may not only prolonged plasma half-life, but also provide enhanced permeability and retention effect, resulting in selective accumulation at tumors and sites of infection and inflammation.

The affinity of EGCG for protein was utilized to load the micellar complexes with an anticancer protein. The protein-loaded complexes demonstrated a much greater anticancer effect than the free protein or the carrier itself. This micellar system may offer improved delivery of various biological molecules, so as to exploit the advantages of the synergistic therapeutic effects and the delivery effects associated with the versatile flavonoid-derivatized carrier.

Example 2

Treatment of Balb/Nude Mice with Micellar Complexes Containing Herceptin

Balb/nude mice were induced with tumours as follows. A 17β-estradiol pellet (0.72 mg, 60 day-release) was administered to each mouse by subcutaneous injection. The following day, a suspension of BT474 cells ($8.1 \times 10^6$ cells/100 uL of Matrigel) was injected subcutaneously in each mouse. Tumours were allowed to develop for two weeks.

Figure 7:
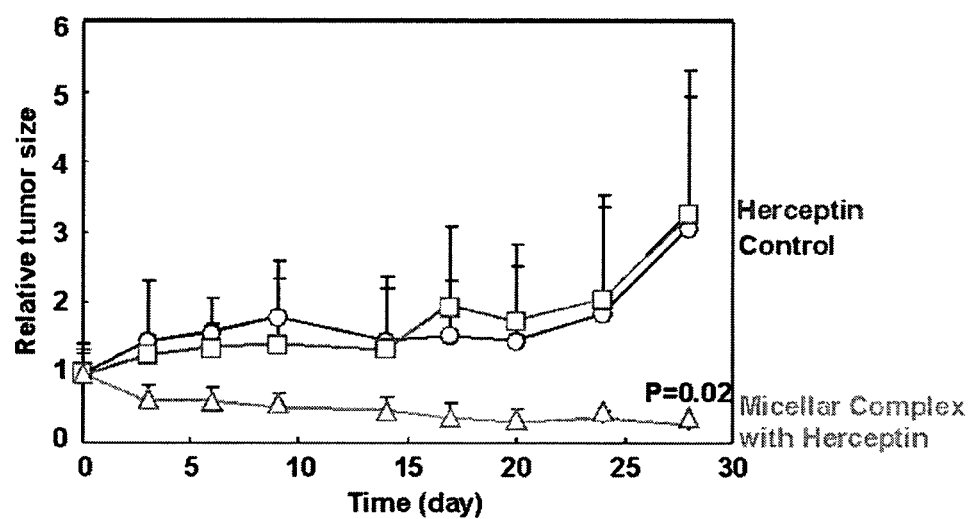
FIG. 7 is a graph depicting tumour size in tumour-containing Balb/nude mice treated twice weekly for one month with (Δ) micellar complex plus Herceptin, (□) Herceptin alone, or (○) PBS control.

Two weeks following injection of the BT474 cells, the mice were treated by intravenous injection, twice weekly for a one-month period, with one of micellar nanocomplexes loaded with Herceptin, Herceptin alone or PBS as a control. After the treatment regimen, tumour size was assessed. The results are shown in FIG. 7.

As can be understood by one skilled in the art, many modifications to the exemplary embodiments described herein are possible. The invention is intended to encompass all such modification within its scope, as defined by the claims.

All documents referred to herein are fully incorporated by reference.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. All technical and scientific terms used herein have the same meaning as commonly understood by one of ordinary skill in the art of this invention, unless defined otherwise.

REFERENCES

Kataoka, K., Kwon, G. S., Yokoyama, M., Okano, T. & Sakurai, Y. Block copolymer micelles as vehicles for drug delivery. *J. Control. Release* 24, 119-132 (1993).

Otsuka, H., Nagasaka, Y. & Kataoka, K. Pegylated nanoparticles for biological and pharmaceutical applications. *Adv. Drug Deliv. Rev.* 55, 403-419 (2003).

Kakizawa, Y. & Kataoka, K. Block copolymer micelles for delivery of gene and related compounds. *Adv. Drug Delivery Rev.* 54, 203-222 (2002).

Lee, E. S., Na, K. & Bae, Y. H. Polymeric micelle for tumor pH and folate-mediated targeting. *J. Control. Release* 91, 103-113 (2003).

Farokhzad, O. C., Jon, S., Khademhosseini, A., Tran, T.-N. T., LaVan, D. A. & Langer, R. Nanoparticle-aptamer bioconjugates: A new approach for targeting prostate cancer cells. *Cancer Res.* 64, 7668-7672 (2004).

Gref, R., Minamitake, Y., Peracchia, M. T., Trubetskoy, V., Torchilin, V. & Langer, R. Biodegradable long-circulating polymeric nanospheres. *Science* 263, 1600-1603 (1994).

Duncan, R. The dawning era of polymer therapeutics. *Nature Rev.* 2, 347-360 (2003). Hubbell, J. Enhancing drug function. *Science* 300, 595-596 (2003).

Kopecek, J., Kopeckova, P., Minko, T. & Lu, Z. HPMA copolymer-anticancer drug conjugates: Design, activity, and mechanism of action. *Eur. J. Pharm. Biopharm.* 50, 61-81 (2000).

Gordon, A. N., Fleagle, J. T., Guthrie, D., Parkin, D. E., Gore, M. E. & Lacave, A. J. Recurrent epithelial ovarian carcinoma: A randomized phase III study of pegylated liposomal doxorubicin versus topotecan. *J. Clin. Oncol.* 19, 3312-3322 (2001).

Cao, Y. & Cao, R. Angiogenesis inhibited by drinking tea. *Nature* 398, 381 (1999). Jankun, J., Selman, S. H., Swiercz, R. & Skrzypczak-Jankun, E. Why drinking green tea could prevent cancer. *Nature* 387, 561 (1997).

Garbisa, S., Biggin, S., Cavallarin, N., Sartor, L., Benelli, R. & Albini, A. Tumor invasion: Molecular shears blunted by green tea. *Nature Med.* 5, 1216 (1999).

Nance, C. L. & Shearer, W. T. Is green tea good for HIV-1 infection? *J. Allergy Clin. Immunol.* 112, 851-853 (2003).

Tachibana, H., Koga, K., Fujimura, Y. & Yamada, K. A receptor for green tea polyphenol EGCG. *Nature Struct. Mol. Biol.* 11, 380-381 (2004).

Mei, Y., Qian, F., Wei, D. & Liu, J. Reversal of cancer multidrug resistance by green tea polyphenols. *J. Pharm. Pharmacol.* 56, 1307-1314 (2004).

Kuroda, Y. & Hara, Y. Antimutagenic and anticarcinogenic activity of tea polyphenols. *Mutat. Res.* 436, 69-97 (1999).

Bordoni, A., Hrelia, S., Angeloni, C., Giordano, E., Guarnieri, C., Caldarera, C. M. & Biagi, P. L. Green tea protection of hypoxia/reoxygenation injury in cultured cardiac cells. *J. Nutr. Biochem.* 13, 103-111 (2002).

Yang, C. S. & Wang, Z.-Y. Tea and cancer. *J. Natl. Cancer Inst.* 85, 1038-1049 (1993).

Kuzuhara, T., Sei, Y., Yamaguchi, K., Suganuma, M. & Fujiki, H. DNA and RNA as new binding targets of green tea catechins. *J. Biol. Chem.* 281, 17446-17456 (2006).

Matsumura, Y. & Maeda, H. A new concept for macromolecular therapeutics in cancer chemotherapy: Mechanism of tumoritropic accumulation of proteins and the antitumor agent smancs. *Cancer Res.* 46, 6387-6392 (1986).

What is claimed is:

1. A micellar nanocomplex comprising:
   trastuzumab; and
   a conjugate of:
   (i) aldehyde-terminated polyethylene glycol; and
   (ii) a flavonoid that is either monomeric (−)-epigallocatechin gallate or oligomeric (−)-epigallocatechin gallate,
   the micellar nanocomplex having the polethylene glycol conjugated at the C6 and/or the C8 position of the A ring of the flavonoid by attachment of the polyethylene glycol via reaction of the free aldehyde group with the C6 and/or C8 position of the A ring of the flavonoid, and exhibiting an anti-cancer effect on a cell as a result of a synergistic effect between the anti-cancer effect of the trastuzumab and the anti-cancer effect of the flavonoid,
   wherein when the flavonoid is monomeric (−)-epigallocatechin gallate, the micellar nanocomplex further comprises non-conjugated oligomeric (−)-epigallocatechin gallate in an inner core of the micellar nanocomplex,
   wherein the trastuzumab is complexed with either the conjugated or non-conjugated oligomeric (−)-epigallocatechin gallate, whichever is present.

2. The micellar nanocomplex of claim 1 wherein the aldehyde-terminated polyethylene glycol is conjugated to oligomeric (−)-epigallocatechin gallate.

3. The micellar nanocomplex of claim 2, wherein the oligomeric (−)-epigallocatechin gallate is formed from (−)-epigallocatechin gallate monomers that have been oligomerized through enzyme-catalyzed oxidative coupling.

4. The micellar nanocomplex of claim 2, wherein the oligomeric (−)-epigallocatechin gallate is formed from (−)-epigallocatechin gallate monomers that have been oligomerized through aldehyde-mediated oligomerization.

5. The micellar nanocomplex of claim 2, wherein the oligomeric (−)-epigallocatechin gallate is formed from (−)-epigallocatechin gallate monomers that have been oligomerized through a carbon-carbon linkage between the C6 or C8 position on the A ring of a first monomeric unit to the C6 or C8 position on the A ring of a second monomeric unit.

6. The micellar nanocomplex of claim 1 wherein the aldehyde-terminated polyethylene glycol is conjugated to monomeric (−)-epigallocatechin gallate and the micellar nanocomplex comprises an inner core containing non-conjugated oligomeric (−)-epigallocatechin gallate.

7. The micellar nanocomplex of claim 6, wherein the oligomeric (−)-epigallocatechin gallate is formed from (−)-epigallocatechin gallate monomers that have been oligomerized through enzyme-catalyzed oxidative coupling.

8. The micellar nanocomplex of claim 6, wherein the oligomeric (−)-epigallocatechin gallate is formed from (−)-epigallocatechin gallate monomers that have been oligomerized through aldehyde-mediated oligomerization.

9. The micellar nanocomplex of claim 6, wherein the oligomeric (−)-epigallocatechin gallate is formed from (−)-epigallocatechin gallate monomers that have been oligomerized through a carbon-carbon linkage between the C6 or C8 position on the A ring of a first monomeric unit to the C6 or C8 position on the A ring of a second monomeric unit.

10. A pharmaceutical composition comprising the micellar nanocomplex according to claim 1.

11. A pharmaceutical composition comprising the micellar nanocomplex according to claim 2.

12. A pharmaceutical composition comprising the micellar nanocomplex according to claim 6.

13. A method of delivering trastuzumab to a cell comprising contacting the micellar nanocomplex of claim 1 with the cell.

14. The method according to claim 13, wherein the cell is in vitro.

15. The method according to claim 13, wherein the cell is in vivo and the method comprises administering the micellar nanocomplex to a subject in need of anti-cancer treatment.

* * * * *